United States Patent [19]
Hirsch

[11] Patent Number: 5,904,916
[45] Date of Patent: May 18, 1999

[54] USE OF ODORANTS TO ALTER LEARNING CAPACITY

[76] Inventor: Alan R. Hirsch, 180 East Pearson, #4702, Chicago, Ill. 60611

[21] Appl. No.: 08/610,730

[22] Filed: Mar. 5, 1996

[51] Int. Cl.$^6$ ..................................................... A61K 9/12
[52] U.S. Cl. ........................... 424/45; 424/401; 424/402; 424/489; 424/76.1; 424/DIG. 5; 424/78.02; 514/937; 514/938; 514/963
[58] Field of Search ............................. 424/45, 401, 402, 424/76.1, DIG. 5, 78.02, 195.1, 489; 514/937, 938, 963

[56] References Cited

U.S. PATENT DOCUMENTS 5,759,521  6/1998  Hirsch ........................................ 424/47

OTHER PUBLICATIONS

J. Borden, "This story stinks, but it might be quite lucrative, "*Crain's Chicago Business* , Metro Chicago's Business Authority (Dec. 2–8, 1991).

A.R. Hirsch, *Advances in Consumer Research* 19:390–395 (1992).

Hirsch, A.R. and L.H. Johnston, "Odors and Learning," The 17th Annual Meeting of the American Academy of Neurological and Orthopaedic Medicine and Surgery, Las Vegas, Nevada, Sep. 11, 1993, 35 pp.

J.R. King, "Anxiety Reduction Using Fragrances," in *The Psychology and Biology of Fragrance*, pp. 147–165, Van Toller & Dodd (eds.), Chapman and Hall, Ltd., London (1988).

A.R. Hirsch, "Enhancement of Learning with a Floral Odor," APA Annual Meeting Philadelphia, Pennsylvania, May 21–26, 1994, Abstract No. NR655, p. 227.

A. R. Genuaro. (1985). Remington's Pharmaceutical Sciences (17$^{th}$ edition). Mack Pub., pp. 1670–1677.

*Primary Examiner*—Raj Bawa
*Attorney, Agent, or Firm*—Godfrey & Kahn, S.C.

[57] ABSTRACT

The invention provides a method for enhancing learning in a person by the administration of a mixed-floral odorant. The odorant can be used as an adjuvant to improve learning and as an aid in education, and for rehabilitation of patients diagnosed with pathologically-induced learning disabilities.

13 Claims, No Drawings

USE OF ODORANTS TO ALTER LEARNING CAPACITY

BACKGROUND OF THE INVENTION

In order to compete in today's rapidly changing technologies and constant flow of new information, it is important to be able to quickly understand and appreciate various facts and information. The ability to learn information and perform tasks is important for children and adults alike, in order to succeed in school and on the job, and operate successfully in one's daily activities. Therefore, it would be beneficial to an individual be able to assimilate and understand new information faster and more proficiently.

Little information has been generated on the effects of odors on learning behavior. In one study, the odors of lavender and cloves were evaluated for their possible impact on learning. The results showed that those odorants did not affect memory or cognition, and that the odor of lavender actually impaired performance of arithmetic tasks. Ludvigson, H. W. and Rottman, T. R., *Chemical Senses* 14:525–536 (1989).

Accordingly, an object of the invention is to provide a method of enhancing a person's capacity for learning a task and/or other information. Another object is to provide means for altering a person's learning capacity that is in a form that is portable and can be easily carried or transported by the user for use at a remote location. Yet another object is to provide such a method and device that will be minimally disruptive to others who are in close proximity to the user.

SUMMARY OF THE INVENTION

These and other objects are achieved by the present invention which is directed to a method for enhancing the learning performance of a human through the delivery of an odorant substance for inhalation. In particular, the method involves delivering an amount of a substance having the characteristics of a mixed-floral odorant substance to the animal for inhaling to cause the capacity to learn and retain information to increase.

The mixed-floral odorant when administered to a person can alter the person's ability to learn and perform various tasks involving, for example, spatial analysis, motor control, alertness and/or concentration for an extended period of time, the manipulation of numbers, spatial memory, and/or to decrease a tendency to shift attention from one subject to another. Furthermore, the odorant can act to intensify "practice effect" in the process of memorizing new information. The mixed floral odorant is useful as an adjuvant to improve learning and as an aid in education, rehabilitation of patients diagnosed with pathologically-induced learning disabilities, and in psychotherapy for patients suffering from stroke or senile dementia of the Alzheimer's type, for example.

DETAILED DESCRIPTION OF THE INVENTION

According to the invention, it was found that by administering a particular mixed-floral odorant substance, a person's ability to learn a new task, including the assimilation of new information, was enhanced. It was found that administering the mixed-floral odorant significantly reduced the amount of time required to learn a task involving, for example, spatial analysis and memory, motor control and alertness and concentration. Such effect was observed by testing a subject, for example, according to the Halsted-Reitan Neuropsychological Test Battery, a trail-making sub-test that tests a subject for their ability to determine the quickest path in a maze.

The mixed-floral odorant is a formulation of floral odorants preferably composed of a fresh, citrus, herbaceous, fruity, and floral odorant that will cause an enhancement in learning capacity of a subject. A useful mixed-floral odorant is a synthetic odorant commercially available, for example, from International Flavors and Fragrances, Inc. (IFF), New York, N.Y., as Mixed-Floral Odorant IFF No. 2635-AS.

According to the method, the mixed-floral odorant is administered to the subject for sniffing and inhalation into the nasal passageway, to deliver an amount of the odorant effective to enhance their learning capacity, which is a suprathreshold level of the scent but not so high as to become an irritant.

An odorant is presented at a suprathreshold level when the decismel level or concentration of the odorant is high enough to be detected by a normosmic individual. At its irritative level, the odorant quantity is so high and intense that the odorant stimulates predominantly the trigeminal nerve (for pain) rather than the olfactory nerve and, hence, is perceived as unpleasant, noxious or painful. The irritation threshold of the patient is the lowest concentration of the substance that causes immediate stinging or burning sensations in the nose, or stinging or lacrimation of the eye. (See, J. F. Gent, in *Clinical Measurement of Taste and Smell*, pages 107–166, H. L. Meiselman et al. (eds), 602 pp., MacMillan, NY (1986); R. L Doty et al., *Ann. Neurol.* 25: 166–171 (1989); E. Koss et al., *Neurology* 38: 1228–1232 (1988); R. Doty, *The Smell Identification Test: Administration Manual* 1983: 13–14, Philadelphia: Sensonics, Inc. (1983)).

The precise magnitude of a loss of smell may be determined by means of an odor threshold test. According to that test, an odorant substance such as butyl alcohol, phenyl ethyl alcohol or pyridine, is combined in an odorless liquid medium to provide a series of dilutions, or binary steps, of the odorant. For each successive binary step up the dilution scale, the odorant is present, for example, at one half the concentration of the preceding step. The highest concentration of the odorant usually provides the substance at an irritant level. The patient is presented with the series of dilutions in ascending order, and is asked to compare each dilution step to at least one control stimulus, such as odorless propylene glycol.

As used herein, a "normosmic" individual is able to detect the odor of an odorant substance without irritant sensations when the substance is presented at a concentration within a range of the average normal threshold for the substance. A "hyposmic" individual is one who has a reduced capacity of the olfactory nerve being able to detect an odorant substance by its odor at a concentration, or decismel level, above that of a normosmic individual yet below its irritant concentration level. An "anosmic" individual is one who has essentially no olfactory nerve capacity being unable to detect the odor of the odorant substance, but has trigeminal nerve function, being able to detect an odorant substance by means of irritant, tingling sensations when it is present at an irritant concentration. A patient who is able to detect pyridine vapor by means of irritant, tingling sensations caused by stimulation of the trigeminal nerve, but who cannot distinguish a pyridine odor at a lower concentration without such sensation, is considered to be anosmic having no olfactory nerve sensitivity.

The effect of the mixed-floral odorant can be assessed objectively by administering a test to the subject repetitively to measure their initial learning performance on a task, and then re-testing the individual's ability to learn a similar task repetitively after being given the odorant, or vice-versa. The effectiveness of the mixed-floral odorant on the subject can be observed by comparing the amount of time required for the person to learn a task before and after inhaling the odorant.

Administration of the mixed-floral odorant to a subject will improve learning of a task such that, in subsequent undertakings, a normosmic person for whom the odor is hedonically positive, is able to complete the task in less time compared to the initial undertaking of the task. Preferably, a normosmic person administered the odorant shows an improvement from a first try to a third try of a task of about twice the speed for completing the task without the odorant. Preferably, a normosmic person given the mixed-floral odorant will complete a task by about 25–35% less time on a third try, or about 30% less time, compared to the initial undertaking of the task. A normosmic subject not given the mixed-floral odorant is able to reduce the time needed to complete a task on a third try compared to the initial try by only about 12–15% less time, averaging about 14% less time.

A normosmic person who finds the odorant hedonically positive is also able to complete the task faster on a third try when administered the odorant compared to normosmics who find the odorant hedonically negative. For normosmics who consider the odor hedonically negative, task completion time of a third subsequent attempt is about 9–10% less time with the mixed-floral odorant and an about 8% reduction without the odorant.

The use of the mixed-floral odorant is useful in enhancing learning in a person with a primary learning disability or a pathologically-induced learning disability. Examples of primary learning disabilities include dyslexia and attention deficit disorder (ADD). Examples of pathological conditions that can induce a learning disability include stroke, head trauma, senile dementia of the Alzheimer's type, multi-infarct dementia, Huntington's chorea, Parkinson's disease, and progressive supranuclear palsy.

The odorant can be administered to improve the learning capacity of an employee at work, a student in an educational setting, and the like, who has normal learning capacity or a primary learning disability; to assist in the rehabilitation of a patient with a pathologically-induced learning disability; and to increase the learning of tasks such as map localization, geography, object manipulation, and the like.

The mixed-floral odorant can be delivered in the form of a liquid solution, aerosol spray, solid, microcapsules, or other suitable form to deliver a suprathreshold amount of the odorant for sniffing by the person. The odorant substance can be administered in combination with an odorless liquid carrier such as mineral oil or water, and can be formulated with a viscosity effective to allow for aerosolization. The odorant can be dispensed, for example, by means of a cloth material that is coated with the odorant, as a solid or liquid form contained in a capped vessel, from an aerosol or pump-type spray device, as a nasal spray, by opening a blister pack or scratch-and-sniff odor patch containing the odorant in the form of microspheres, from a pen-like dispenser containing a liquid form of the odorant adsorbed to a wicking material, and the like.

To deliver the odorant, the user can employ a device that is portable and minimally disruptive of bystanders. The odorant can also be administered to a group of people within a confined area, for example, by pumping air containing the mixed-floral odorant through an air vent, spraying the odorant substance into the air as a mist or dry powder using an aerosol or non-aerosol spray, and the like.

The multi-floral odorant substance can be packaged as a part of an article of manufacture, or kit, for use in enhancing learning. The kit can include in association, for example, an effective amount of the mixed-floral odorant substance in a non-reactive, biocompatible carrier and/or optional additives as desired such as an antioxidant, preservative, and the like; and means for containing the odorant such as a vial, jar, pouch, can, bottle, cloth, aerosol can, blister pack, scratch-and-sniff odor patch, pen-like device, and the like. The containing means can include means for spraying by aerosolization or pumping. The kit can further include means for instructing the user about the use of the multi-floral odorant substance to enhance a person's learning ability, in the form of a label or tag attached to the packaging and/or a printed package insert. The parts of the kit can be contained or separately packaged within a packaging material, such as a box or bag.

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references are incorporated by reference herein.

EXAMPLE

Subjects. Twenty-two subjects, 12 males and 10 females ranging from 15–65 years of age (mean 36, median 34) participated in the experiment. All subjects were given the Chicago Smell Test and the Pyridine-Threshold Test of Amoore to establish that their olfactory ability was normal (A. R. Hirsch and M. B. Gotway, *Chemical Senses* 18(5) :570–571 (1993); A. R. Hirsch, M. B. Gotway and A. T. Harris, *Chemical Senses* 18(5):571 (1993); A. R. Hirsch and D. R. Cain, *Chemical Senses* 17(5):p. 642–3 (1992); and Amoore et al., *Rhinology* 21:49–54 (1983)).

Test and Procedure. Two trail-making (maze) tests modified from the trail-making subtest of the Halsted-Reitan Neuropsychological Test Battery used to detect neurological problems were used (Reitan, R. M., "Halsted-Reitan Neuropsychological Test Battery," Neuropsychology Laboratory, University of Arizona, Tucson, Ariz. (1979)). Trail B was used, but the numbers were randomly changed on one of the mazes to avoid any cross-over learning effect.

Subjects were told that they would be tested for their ability to complete the maze test while wearing masks. The masks were made of 3-M paper surgical masks, and were designed to cover the nose and mouth. Prior to testing, subjects accustomed themselves to the masks or the distracting effect of any odor by wearing an unscented or scented mask for one minute prior to testing. Subjects then underwent testing in randomized, double-blinded fashion, with two trail-making (maze) tests modified as described above. Each subject underwent the trials twice: once while wearing an unscented mask and once wearing a floral-scented mask. The scented masks were prepared by applying one drop of the mixed floral odorant, resulting in a suprathreshold level of scent (i.e., a level that was high enough that subjects could detect an odor was present).

The mixed-floral odorant was an artificial floral odor IFF No. 2635-AS from International Flavors and Fragrances, Inc. (IFF), New York, N.Y.

The order of presentation of the scented versus unscented masks was random, but the order of maze presentation was constant. Subjects always performed first the trail-making subtest of the Halsted-Reitan Battery, Part B (three times), followed by the modified trail-making subtest of the Halsted-Reitan Battery, Part B (three times). Each subject attempted the set of two mazes a total of three times sequentially with each mask. The time required to complete each trial was measured.

Statistical Analysis. The percent change in the time required to complete the second and third trials compared to the first trial was analyzed using Mann-Whitney U, Spearman rank correlation, and Wilcoxon rank sum tests for nonparametric data.

Results. The characteristics of the 22 volunteers are shown in Table 1 below. Subject number 16 failed the pyridine-threshold test of Amoore and was therefore considered impaired in olfactory ability. Of the 21 normosmic subjects, 10 subjects considered the mixed-floral scent hedonically positive. The other 11 subjects considered the odorant either neutral or hedonically negative.

TABLE 1

Characteristics of Subjects

| Subject No. | Sex | Age | Smoker | Floral Odor Hedonics | Olfactory Test of Amoore Pyridine Threshold (decismels)* |
|---|---|---|---|---|---|
| 1. | M | 23 | N | positive | 25 |
| 2. | F | 43 | Y | negative | 25 |
| 3. | M | 43 | N | positive | 25 |
| 4. | M | 32 | N | negative | 25 |
| 5. | M | 15 | N | negative | 25 |
| 6. | F | 37 | Y | positive | 25 |
| 7. | F | 26 | N | positive | 25 |
| 8. | F | 35 | N | positive | 25 |
| 9. | M | 26 | N | positive | 25 |
| 10. | F | 31 | N | indifferent | 25 |
| 11. | F | 35 | Y | positive | 25 |
| 12. | F | 55 | Y | indifferent | 25 |
| 13. | F | 25 | Y | positive | 25 |
| 14. | M | 39 | Y | indifferent | 25 |
| 15. | M | 25 | N | indifferent | 25 |
| 16. | M | 23 | N | positive | 25 |
| 17. | M | 26 | N | positive | 25 |
| 18. | M | 33 | Y | negative | 25 |
| 19. | M | 62 | N | negative | 25 |
| 20. | F | 54 | Y | positive | 25 |
| 21. | F | 38 | N | negative | 25 |
| 22. | M | 65 | N | negative | 25 |

*Normal range is −25 to +25 decismels.

Table II below shows the amount of time in seconds taken by each subject to complete each of the three trials both with the scented masks and with unscented masks.

TABLE II

| | | UNSCENTED TRIALS | | | | | | SCENTED TRIALS | | | | | |
|---|---|---|---|---|---|---|---|---|---|---|---|---|---|
| Subj. No. | Order of Presentation | Trial 1 sec. | Trial 2 sec. | Trial 3 sec. | % delta trial 1–2 | % delta trial 2–3 | % delta trial 1–3 | Order of Presentation | Trial 1 sec. | Trial 2 sec. | Trial 3 sec. | % delta trial 1–2 | % delta trial 2–3 | % delta trial 1–3 |
| 1. | first | 38.4 | 27.7 | 25.7 | −27.9% | −7.2% | −33.1% | second | 53.1 | 30.6 | 30.2 | −42.4% | −1.3% | −43.1% |
| 2. | second | 46.2 | 57.2 | 41.9 | +23.8% | −26.7% | −9.3% | first | 54.7 | 43.3 | 56.7 | −20.8% | +30.9% | +3.7% |
| 3. | first | 72.5 | 57.9 | 51.9 | −20.1% | −10.5% | −28.4% | second | 74.2 | 53.4 | 42.4 | −28.0% | −20.6% | −42.9% |
| 4. | second | 38.0 | 38.0 | 32.2 | 0% | −15.3% | −15.3% | first | 49.6 | 37.4 | 34.4 | −24.6% | −8.0% | −30.6% |
| 5. | first | 82.8 | 57.9 | 64.7 | −30.1% | +11.7% | −21.9% | second | 53.6 | 48.6 | 44.8 | −9.3% | −7.8% | −16.4% |
| 6. | second | 33.9 | 32.0 | 31.4 | −5.6% | −1.9% | −7.4% | first | 51.3 | 35.3 | 42.9 | −31.2% | +21.5% | −16.4% |
| 7. | first | 50.4 | 40.6 | 40.1 | −19.4% | −1.2% | −20.4% | second | 44.1 | 46.9 | 42.7 | +6.3% | −9.0% | −3.2% |
| 8. | second | 35.0 | 33.1 | 43.2 | −5.4% | +30.5% | +23.4% | first | 34.0 | 26.4 | 24.8 | −22.4% | −6.1% | −27.1% |
| 9. | first | 32.8 | 26.8 | 33.9 | −18.3% | +26.5% | +3.4% | second | 34.5 | 25.1 | 25.1 | −27.2% | 0% | −27.2% |
| 10. | second | 60.1 | 53.2 | 40.4 | −11.5% | −24.1% | −32.8% | first | 59.1 | 87.1 | 59.2 | +47.4% | −32.0% | +0.2% |
| 11. | first | 75.1 | 63.1 | 58.0 | −16.0% | −8.1% | −22.8% | second | 67.3 | 43.8 | 42.2 | −34.9% | −3.7% | −37.3% |
| 12. | second | 57.6 | 57.7 | 61.5 | −0.2% | +6.6% | +6.8% | first | 75.5 | 126.4 | 48.4 | +67.7% | −61.8% | −35.9% |
| 13. | first | 55.5 | 63.3 | 44.6 | +14.1% | −29.5% | −19.6% | second | 41.1 | 41.8 | 32.0 | +1.7% | −23.4% | −22.1% |
| 14. | second | 49.5 | 45.8 | 35.3 | −7.5% | −22.9% | −28.7% | first | 52.2 | 53.8 | 48.1 | +3.1% | −10.6% | −7.9% |
| 15. | first | 40.9 | 35.7 | 37.2 | −12.7% | −4.2% | −9.0% | second | 28.3 | 26.0 | 33.7 | −8.1% | +29.6% | +19.1% |
| 16. | second | 37.5 | 38.9 | 25.3 | +3.7% | −35.0% | −32.5% | first | 49.3 | 31.5 | 38.6 | −36.1% | +22.5% | −21.7% |
| 17. | second | 44.3 | 46.8 | 39.4 | +5.6% | −15.8% | −11.1% | first | 74.9 | 45.3 | 42.6 | −39.5% | −6.0% | −43.1% |
| 18. | first | 93.8 | 91.9 | 77.4 | −2.0% | −15.9% | −17.5% | second | 77.5 | 55.8 | 54.9 | −28.0% | −1.6% | −29.2% |
| 19. | second | 47.9 | 59.9 | 52.8 | +25.1% | −11.9% | +10.2% | first | 50.9 | 58.6 | 64.5 | +15.1% | −10.1% | +26.7% |
| 20. | first | 75.2 | 54.1 | 63.6 | −28.1% | +17.6% | −15.4% | second | 70.1 | 44.0 | 43.1 | −37.2% | −2.0% | −38.5% |
| 21. | second | 46.2 | 39.3 | 56.6 | −14.9% | +44.0% | +22.5% | first | 60.3 | 47.8 | 52.8 | −20.7% | +10.5% | −12.4% |
| 22. | first | 56.3 | 45.8 | 58.9 | −18.7% | +28.6% | +4.6% | second | 59.9 | 36.8 | 44.3 | −38.6% | +20.4% | −26.0% |

As shown in Table III below, normosmics who found the odor hedonically positive (n=10) displayed a significant improvement in learning in the presence of the mixed-floral odorant. On subsequent trials, these subjects learned to complete the tasks in an average of 30.1% less time in the presence of the odor. In the trials without the odor, they learned to complete the tasks on an average of only 13.1% less time. In other words, they learned to complete the tasks on an average of 17% less time in the presence of the mixed-floral odorant than in the non-odorized condition.

(essential oils), citrus (IFF 2898-HS), parsley (Aroma Tech 236938), and spearmint (essential oils), showed no effect on learning time in the trail-making test even though the subjects considered those odorants hedonically positive. This shows that positive hedonics alone are insufficient to improve learning. By comparison, the mixed floral scent caused a significant improvement in learning. This shows that the characteristics of the odor are essential.

Learning involves a multitude of integrated neurologic functions and, although not wished to be held to any theory,

TABLE III

Normosmic Subjects with Positive Hedonics

| | | UNSCENTED TRIALS | | | | | | SCENTED TRIALS | | | | | |
|---|---|---|---|---|---|---|---|---|---|---|---|---|---|
| Subj. No. | Order of Presentation | trial 1 sec. | trial 2 sec. | trial 3 sec. | % delta trial 1–2 | % delta trial 2–3 | % delta trial 1–3 | Order of Presentation | trial 1 sec. | trial 2 sec. | trial 3 sec. | % delta trial 1–2 | % delta trial 2–3 | % delta trial 1–3 |
| 1. | first | 38.4 | 27.7 | 25.7 | −27.9% | −7.2% | −33.1% | second | 53.1 | 30.6 | 30.2 | −42.4% | −1.3% | −43.1% |
| 3. | first | 72.5 | 57.9 | 51.9 | −20.1% | −10.5% | −28.4% | second | 74.2 | 53.4 | 42.4 | −28.0% | −20.6% | −42.9% |
| 6. | second | 33.9 | 32.0 | 31.4 | −5.6% | −1.9% | −7.4% | first | 51.3 | 35.3 | 42.9 | −31.2% | +21.5% | −16.4% |
| 7. | first | 50.4 | 40.6 | 40.1 | −19.4% | −1.2% | −20.4% | second | 44.1 | 46.9 | 42.7 | +6.3% | −9.0% | −3.2% |
| 8. | second | 35.0 | 33.1 | 43.2 | −5.4% | +30.5% | +23.4% | first | 34.0 | 26.4 | 24.8 | −22.4% | −6.1% | −27.1% |
| 9. | first | 32.8 | 26.8 | 33.9 | −18.3% | +26.5% | +3.4% | second | 34.5 | 25.1 | 25.1 | −27.2% | 0% | −27.2% |
| 11. | first | 75.1 | 63.1 | 58.0 | −16.0% | −8.1% | −22.8% | second | 67.3 | 43.8 | 42.2 | −34.9% | −3.7% | −37.3% |
| 13. | first | 55.5 | 63.3 | 44.6 | +14.1% | −29.5% | −19.6% | second | 41.1 | 41.8 | 32.0 | +1.7% | −23.4% | −22.1% |
| 17. | second | 44.3 | 46.8 | 39.4 | +5.6% | −15.8% | −11.1% | first | 74.9 | 45.3 | 42.6 | −39.5% | −6.0% | −43.1% |
| 20. | first | 75.2 | 54.1 | 63.6 | −28.1% | +17.6% | −15.4% | second | 70.1 | 44.0 | 43.1 | −37.2% | −2.0% | −38.5% |
| | Avg. | 51.3 | 44.5 | 43.2 | −12.1% | +0.4% | −13.1% | | 54.5 | 39.3 | 36.8 | −25.5% | −5.1% | −30.1% |

Normosmics who found the odorant hedonically negative (n=7) also displayed a slight, but statistically non-significant improvement in learning in the presence of the odorant. An average of 9.9% reduction in time was needed by this group to complete the trial in the presence of the odorant versus 8.2% reduction in time without the odorant.

Results did not differ significantly for the 21 normosmic subjects due to the order of presentation of scented versus unscented masks (p>0.05), the subject's sex (p>0.05), their smoking status (p>0.5), or their ages (p=0.06).

For the subjects who found the odorant hedonically positive, the odorant had the greatest impact on learning from the first to second trial. The average improvement with the scented masks was 25.5% less time for the second trial compared to the first, and with the unscented masks only 12.1% less time (t=9, critical value=8, "=0.05, 2-tail). From the second to the third trial, the average time required was 5.1% less with the scent while the performance with unscented masks actually worsened, requiring slightly more time for the third trial than for the second (t=19, critical value=8, "=0.05, 2-tail). Hence, the presence of the odor continued substantially to improve relative performance from the second to the third trial, while in the absence of odor, performance slightly worsened.

Discussion. Subjects with normal olfactory ability who considered the odorant hedonically positive demonstrated that on subsequent trials they learned to complete the tasks 17% faster on average in the presence of the floral odor than in the non-odorized condition. The improvement was greatest from the first to the second trial. Although the odorant had a diminished effect from the second trial to the third trial, the effect of the odorant remained statistically significant from the second to third trial.

Pre-testing of subjects with other odors, i.e., oriental spice (IFF 2245-HS), baked goods (IFF 2292-AS), lavender the mixed-floral odorant may have facilitated deposition of short term memory, the processing of newly learned material, or the access of these memories for subsequent tasks, or could have facilitated the creation of new strategies for solution of problems. In addition, learning depends upon multiple variables: attention, interest, underlying neurologic substrate, task difficulty, competing environmental distractions, and the inherent baseline emotional state of the organism which is a function of the limbic system. Learning can be impacted by changes in attention (wakefulness), distraction, motivation, and mood.

For example, odors can act as competing stimuli thereby reducing concentration on the task. In that case, the distraction must be overcome before learning can occur. This was not the case with the mixed floral scent.

The odorant may increase the level of motivation in a classical Pavlovian conditioned response such that the odorant stimulus may induce recall of a past behavior or learning situation, and enhance (or hinder) the learning state in an individual who had a positive (or negative) learning experience associated with that smell.

The odorant may also have a direct physiologic impact upon brain structures that are involved in learning, i.e., the hippocampus and cortex. These areas are directly influenced by anatomic projections from the olfactory system. Pathology of these structures that are known to impair learning also affects olfactory ability, as for example with Korsakoff's syndrome, temporal-lobe epilepsy, and schizophrenia (prefrontal cortex). Other more diffuse neurologic diseases that impair both learning and olfaction include senile dementia of the Alzheimer's type and head injury.

The mixed-floral odorant may also modulate the same neurotransmitters that are involved in the processes of both learning and olfaction. Such neurotransmitters include norepinephrine, dopamine, serotonin, acetylcholine, and GABA, as well as the hypophyseal neuropeptides and nonhypophyseal hormones. Examples of hypophyseal hormones include methionine-enkephalin and beta endorphin, and examples of the nonhypophyseal hormones include substance P, neurotensin and cholecystokinin.

Inhalation of odorants may increase norepinephrine discharge from the locus ceruleus, and the compound could act directly as a neurotransmitter to increase learning. Alternatively, norepinephrine could stimulate the reticular activating system, making the individual more alert and thus improve learning. Further, norepinephrine could act indirectly by causing an increase in attention, i.e., stress, secondarily causing an increase in vasopressin level.

Vasopressin, in addition to being released secondary to stress (alertness), may also be released from the olfactory bulb by the direct action of the odorant. This may further enhance alertness and memory, both of which can improve learning.

A third construct, acetylcholine (ACTH) is released when norepinephrine stimulates the reticular activating system, as in response to stress. The release of ACTH increases attention-enhanced learning. ACTH also causes release of cortisol which acts on those structures of the brain that are jointly involved in learning and olfaction. These include the amygdala, piriform cortex and entorhinal cortex. Thus, since a degree of alertness is necessary for learning, the mixed floral odor may have acted to stimulate the reticular activating system.

The mixed floral odorant may also improve learning by inducing a positive feeling which secondarily enhances cognition. It is known that exposure to odors experienced as hedonically positive produces a positive affective state and exposure to odors experienced as hedonically negative produces a negative affective state. Undoubtedly, a positive mood state would directly improve learning.

The odorant may also decrease excess anxiety, an inhibitor of learning, although too much relaxation may impair performance and a less relaxing odor may have an even greater positive effect on learning.

The impact of the mixed floral odorant may also be upon the limbic system itself as with jasmine or lavender odorants. Only one sensory system by definition is included within the limbic system and that is the olfactory system. Hence, the mixed floral odorant may impact on learning through limbic system functioning. Evidence indicates that odor affects mood. An odorant can induce recall of a scene from the past. By directly stimulating the limbic system, the odorant can act as an agent to induce recall, memory and nostalgia, and thus cause a change in learning.

Animal studies also indicate that drugs used to improve olfaction can also improve learning. For example, norepinephrine is a common neurotransmitter to both systems. Amphetamine, a norepinephrine agonist, has been shown to improve learning as well as olfaction in test animals. Similar effects may occur in human pathology. Acetylcholine is a neurotransmitter common to both the learning and olfactory systems, and phosphatidylcholine is known to increase central nervous system acetylcholine levels. Treatment with phosphatidylcholine may improve both functions in patients deficient in acetylcholine, i.e., those with senile dementia of the Alzheimer's type. Phosphatidylcholine has been used to correct both olfactory deficiencies in those with hyposmia and anosmia, and to improve functional ability in those with learning impairments due to senile dementia of the Alzheimer's type.

Likewise, dopamine is a neurotransmitter in both systems. Amantadine, a dopamine agonist may improve olfactory ability in those with olfactory loss and improve overall cognitive ability in those with Parkinson's disease. Another overlapping neurotransmitter is serotonin, dysregulation of which may cause depression. Amitriptyline, a 5HT agonist, improves both learning ability in those with depression and may also improve olfactory ability in those who are hyposmic. Milacemide (proglycine), a learning enhancing drug, may be an olfactory enhancing agent.

The trail-making test is a paradigm for the learning tasks of spatial analyses, motor control, attention shifting, alertness, concentration and number sense (Lishman, W. A., "Psychological Consequences of Cerebral Disorder," In: *Organic Psychiatry*, page 141, Blackwell Scientific Publications, Oxford (1978)). Brain damage at a various locations can impair trail-making, so it is logical that intervention at these locations could improve performance. The mixed floral odorant may have acted at any of these sites to improve learning.

The effect of the mixed floral odorant on improved spatial analysis/orientation is of particular interest. This cognitive process is localized in the right nondominant hemisphere. Likewise, olfaction is predominantly processed in the right nondominant hemisphere. Thus, the use of the mixed floral odorant is particularly useful for learning paradigms that involve the right hemisphere such as solving mazes, spatial design, puzzles, and peg-block tests.

The order of presentation of the scented and unscented masks had no effect on the results. In other words, there was no bias due to whether the odorized or blank mask was presented first. It was anticipated, based on a learning curve, that the second trail-making test would be completed faster even without any effect due to odor. However, no substantially significant improvement occurred with subjects wore the unscented masks.

The subject's sex and smoking status showed no significant effect on their performance in the study. It was anticipated that women and nonsmokers would show greater improvement than males and smokers on the basis that women and nonsmokers have better olfactory ability than males and smokers. This was due, at least in part, to the cognitive task not being sex dependent, and the levels of odorant used being sufficiently suprathreshold.

What is claimed is:

1. A method for enhancing learning in a normosmic person, comprising the following steps:

administering to the person by inhalation a suprathreshold but not irritant amount of a floral odorant; wherein inhaling an amount of said odorant enhances the capacity of said person to learn a task selected from the group consisting of spatial analysis, motor control, alertness, concentration, manipulation of numbers, and retention in memory of spatial orientation; and the amount of odorant administered is effective to enable the person to complete the task on a subsequent undertaking of the task by about 25–35% less time compared to a first undertaking of the task.

2. The method according to claim 1, wherein the odorant is administered in a form selected from the group consisting of a solid or liquid contained in a capped vessel, spray, gas, scented cloth, lotion, cream, perfume, cologne, scratch-and-sniff odor patch containing microcapsules of the odorant, a blister pack containing the odorant, solid air freshener, potpourri, incense, lightbulb ring, candle, and combinations thereof.

3. The method according to claim 1, wherein the odorant is administered as an aerosol spray or nasal spray.

4. A method for enhancing learning in a normosmic person, comprising the steps of:

administering to the person by inhalation a suprathreshold but not irritant amount of a floral odorant to assist in the rehabilitation of a patient diagnosed as having a pathologically-induced learning disability; wherein inhaling an amount of said odorant enhances the capacity of said person to learn a task selected from the group consisting of spatial analysis, motor control, alertness, concentration, manipulation of numbers, and retention in memory of spatial orientation; and the amount of odorant administered is effective to enable the person to complete the task on a subsequent undertaking of the task by about 25–35% less time compared to a first undertaking of the task.

5. The method of claim 4, wherein the patient is diagnosed as having a pathologically-induced learning disability selected from the group consisting of a stroke, head trauma, senile dementia of the Alzheimer's type, multi-infarct dementia, Huntington's chorea, Parkinson's disease, and progressive supranuclear palsy.

6. A method for enhancing learning in a normosmic person, comprising the steps of:

administering to the person by inhalation a suprathreshold but not irritant amount of a floral odorant; said person diagnosed as having a primary learning disability; wherein inhaling an amount of said odorant enhances the capacity of said person to learn a task selected from the group consisting of spatial analysis, motor control, alertness, concentration, manipulation of numbers, and retention in memory of spatial orientation; and the amount of odorant administered is effective to enable the person to complete the task on a subsequent undertaking of the task by about 25–35% less time compared to a first undertaking of the task.

7. The method according to claim 6, wherein the person is diagnosed as having dyslexia or attention deficit disorder.

8. An article of manufacture, comprising, packaged together:

(a) the odorant as recited in claim 1, wherein said odorant when inhaled by a person is effective to enhance the capacity of the person to learn the task; and (b) instructions for use of said odorant according to the method of claim 1.

9. The article of manufacture according to claim 8, wherein said odorant is packaged within a delivery means selected from the group consisting of a vial, jar, pouch, can, bottle, blister pack, and a scratch-and-sniff odor patch containing microcapsules of the odorant.

10. The article of manufacture according to claim 8, wherein said odorant is in a form selected from the group consisting of a cloth scented with said odorant, an aerosol spray, a pump-type spray, a nasal spray, a liquid or solid form of said odorant contained in a vessel having a cap, a liquid or solid form of said odorant contained in a blister pack, and microcapsules of said odorant contained in a scratch-and-sniff odor patch.

11. The article of manufacture according to claim 8, wherein said odorant is in the form of a cream or a cologne.

12. The article of manufacture according to claim 8, wherein said odorant is in a liquid form contained in a dispenser.

13. The article of manufacture according to claim 8, wherein said dispenser contains the odorant adsorbed to a wicking material.

* * * * *